United States Patent [19]

Boussignac et al.

[11] Patent Number: 5,312,339
[45] Date of Patent: May 17, 1994

[54] ENDOPROSTHESIS CATHETER

[76] Inventors: Georges Boussignac, 1 Avenue de Provence; Jean-Claude Labrune, 2, Avenue de Guyenne, both of 92160 Antony, France

[21] Appl. No.: 682,591

[22] Filed: Apr. 8, 1991

[30] Foreign Application Priority Data

Apr. 13, 1990 [JP] Japan .................................. 90 04840

[51] Int. Cl.$^5$ .................................................. A61M 25/00
[52] U.S. Cl. ........................................ 604/96; 604/99; 623/12; 128/4; 606/192
[58] Field of Search ........................... 604/96–103, 604/264, 280; 606/191, 192, 194; 623/10, 112; 128/4, 6

[56] References Cited

U.S. PATENT DOCUMENTS

| | | | |
|---|---|---|---|
| Re. 32,348 | 2/1987 | Peusher | 606/194 |
| 3,996,938 | 12/1976 | Clark, III | 606/192 |
| 4,503,569 | 3/1985 | Dotter | 606/191 |
| 4,650,466 | 3/1987 | Luther | 606/194 |
| 4,681,564 | 7/1987 | Landreneau . | |
| 4,877,031 | 10/1989 | Conway | 604/96 |
| 4,922,905 | 5/1990 | Strecker | 623/12 |
| 5,000,734 | 3/1991 | Baissignac et al. | 606/194 |
| 5,037,392 | 8/1991 | Millstead | 606/191 |
| 5,071,407 | 12/1991 | Termin et al. | 606/194 |
| 5,089,005 | 2/1992 | Harada | 606/192 |
| 5,108,370 | 4/1992 | Wainsky | 604/96 |
| 5,160,321 | 11/1992 | Sahota | 604/96 |

FOREIGN PATENT DOCUMENTS

| | | |
|---|---|---|
| 0275230 | 7/1988 | European Pat. Off. . |
| 2617721 | 1/1989 | France . |
| WO8805671 | 8/1988 | PCT Int'l Appl. . |

Primary Examiner—C. Fred Rosenbaum
Assistant Examiner—Chalin Smith
Attorney, Agent, or Firm—Marshall, O'Toole, Gerstein, Murray & Borun

[57] ABSTRACT

A catheter for a morphological duct is disclosed, comprising an inflatable sleeve surrounding the distal end of said catheter and connected to the proximal end of said catheter by at least one inflating conduit which can be connected to an inflating device and said inflatable sleeve may take on either a deflated state in which it is applied against said distal end of said catheter, or an inflated state in which it is applied by its external wall against the internal wall of said morphological duct, then forming an annular space between its internal wall and said distal end of said catheter.

10 Claims, 2 Drawing Sheets

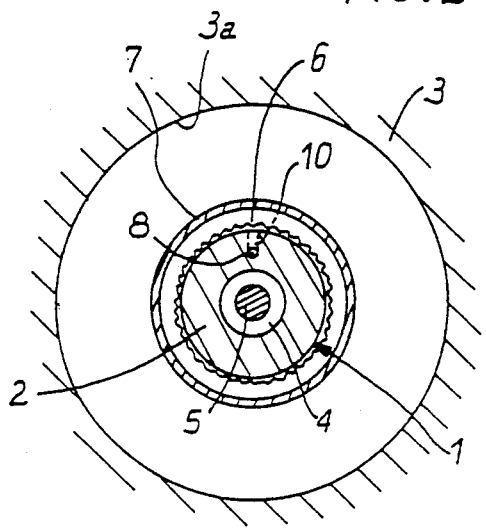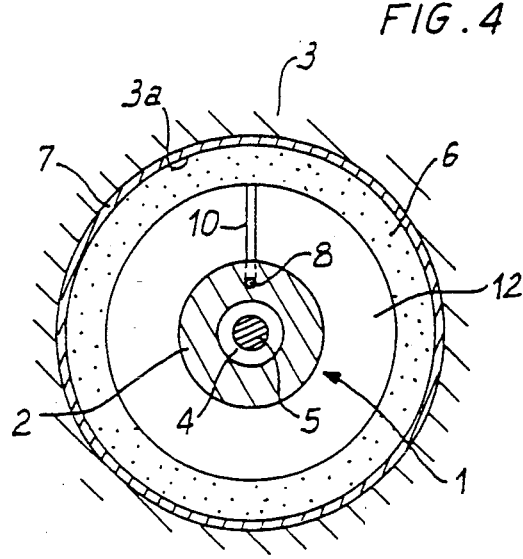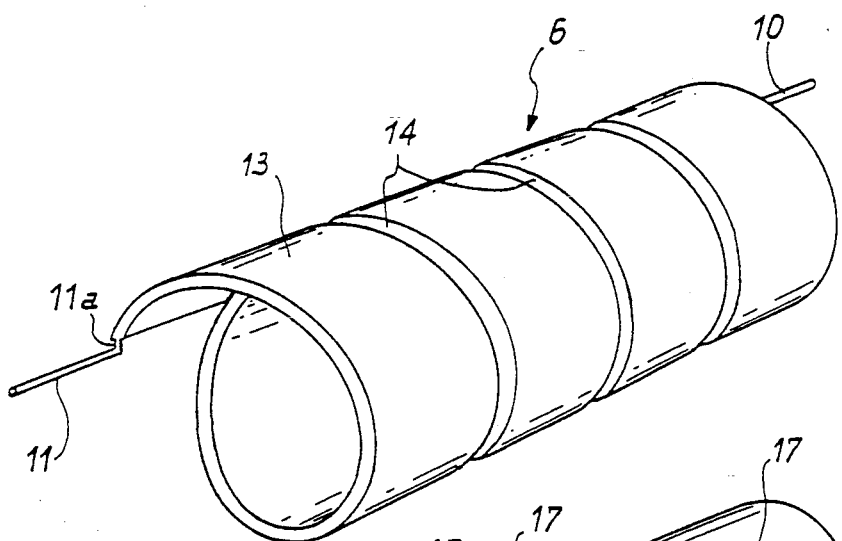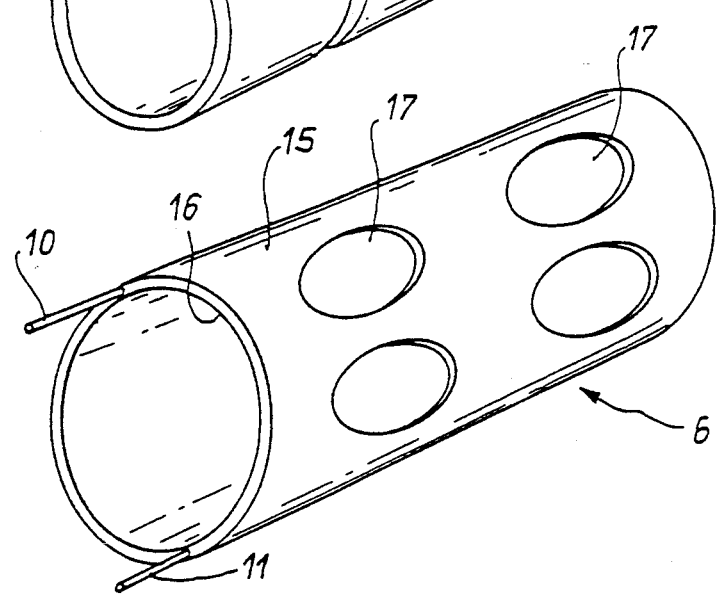

ENDOPROSTHESIS CATHETER

BACKGROUND OF THE INVENTION

The present invention relates to a catheter for a morphological duct capable of positioning an endoprosthesis, temporarily or permanently, inside said morphological duct.

More particularly, although not exclusively, the catheter according to the present invention is intended to end an operation performed with an expansion probe or laser radiation in a morphological duct blocked at least partially by an atheroma. The invention will be more particularly described hereafter with regard to such an application, which must however not be considered as limitative of the invention.

To unblock such a morphological duct, the distal end either of an expansion probe able to expand said atheroma radially or an optical fiber catheter able to conduct laser radiation for eliminating said atheroma is introduced into the morphological duct as far as said atheroma.

It has been noted that, following such radial expansion or such elimination by laser radiation, the wall of the morphological duct has, at the location of the eliminated atheroma, numerous rough portions or membranes favoring the formation of a new atheroma.

SUMMARY OF THE INVENTION

The purpose of the present invention is to overcome this drawback.

For this, according to the present invention, the catheter for a morphological duct is remarkable in that it comprises an inflatable sleeve surrounding the distal end of said catheter and connected to the proximal end of said catheter by at least one inflating conduit which can be connected to an inflating device and in that said inflatable sleeve may take on either a deflated state in which it is applied against said distal end of said catheter, or an inflated state in which it is applied by its external wall against the internal wall of said morphological duct, then forming an annular space between its internal wall and said distal end of said catheter.

Thus, in the deflated state said sleeve may be introduced without difficulty inside said morphological duct, to the level of an eliminated atheroma, via said catheter then, once positioned, it may be inflated so as to form in situ a prosthesis having an annular cross section able to cover, and so inhibit, the rough portions and other elements likely to initiate the formation of a new atheroma.

It will be noted that, if required, the inflatable sleeve may also be used as means for radially expanding said morphological duct, in the place of the inflatable balloons with which expansion probes are generally provided, and that in all circumstances—whether there is an atheroma or not—the sleeve of the catheter according to the present invention forms a local reinforcement of said morphological duct.

Preferably, so that said inflatable sleeve is compressed against the distal end of said catheter, when said sleeve is deflated a resilient membrane is provided surrounding said sleeve. Thus, said sleeve is compressed radially in the direction of the catheter, which facilitates introduction of the latter into the morphological duct. The radial expansion of the sleeve then takes place against the resilient action of said membrane.

Such a membrane is formed of a biocompatible implantable material, such as silicon or latex. Advantageously, as will be seen further on, this membrane is perforated and may even have the form of a net, so as not to hinder the peripheral blood flow, when the sleeve is itself perforated and is disposed at the intersection of morphological ducts.

Moreover, if the sleeve is intended to form a temporary prosthesis which only keeps its radially expanded form under the action of the pressure exerted by a fluid introduced into the inflating conduit by said inflating device, it can be seen that, when the intake of inflating fluid ceases, said resilient membrane brings the deflated sleeve back into a position gripped round the distal end of the catheter, which allows the catheter and its sleeve to be removed from said morphological duct.

In an advantageous embodiment, said inflating conduit is incorporated in said catheter and is connected to said sleeve by a flexible connection. Thus, said sleeve is firmly secured to said catheter by said connection.

In the case where a permanent prosthesis is desired inside said morphological duct, said sleeve is fed with an inflating fluid capable of rigidifying said sleeve in its inflated state and it is arranged for said flexible connection to be breakable. Thus, after hardening of said inflating fluid, which then gives the sleeve a final rigid form, the catheter may be removed from the morphological duct while leaving said inflated sleeve therein.

Preferably, in addition to the inflating conduit, an inflating fluid discharge conduit is provided connecting said sleeve to the proximal end of the catheter. Thus, it is possible to perfectly control the fluid contents of the sleeve and to remove possible impurities or gas which may exist in the sleeve by a complete draining. It is then advantageous for this draining conduit, like the inflating conduit, to be incorporated in said catheter and to be connected to said sleeve by a flexible connection. In the case of a permanent prosthesis, this latter flexible connection is also breakable.

Advantageously, the sleeve is formed by a tube wound in a helical coil or by a double-walled tube. So as to allow homogeneous flow through the wall of the sleeve, said turns are not made jointing or openings are formed in the double-walled tube.

BRIEF DESCRIPTION OF THE DRAWINGS

The figures of the accompanying drawings will better show how the invention may be put into practice. In these figures, identical references designate similar elements.

FIG. 2 is a cross section though line II—II of FIG. 1;

FIG. 4 is a cross section through line IV—IV of FIG. 3;

FIG. 5 shows in enlarged perspective one embodiment of the sleeve, in the form of a coil; and FIG. 6 shows, also in enlarged perspective, a variant of the sleeve according to the present invention.

DESCRIPTION OF THE PREFERRED EMBODIMENTS

Figure 1:
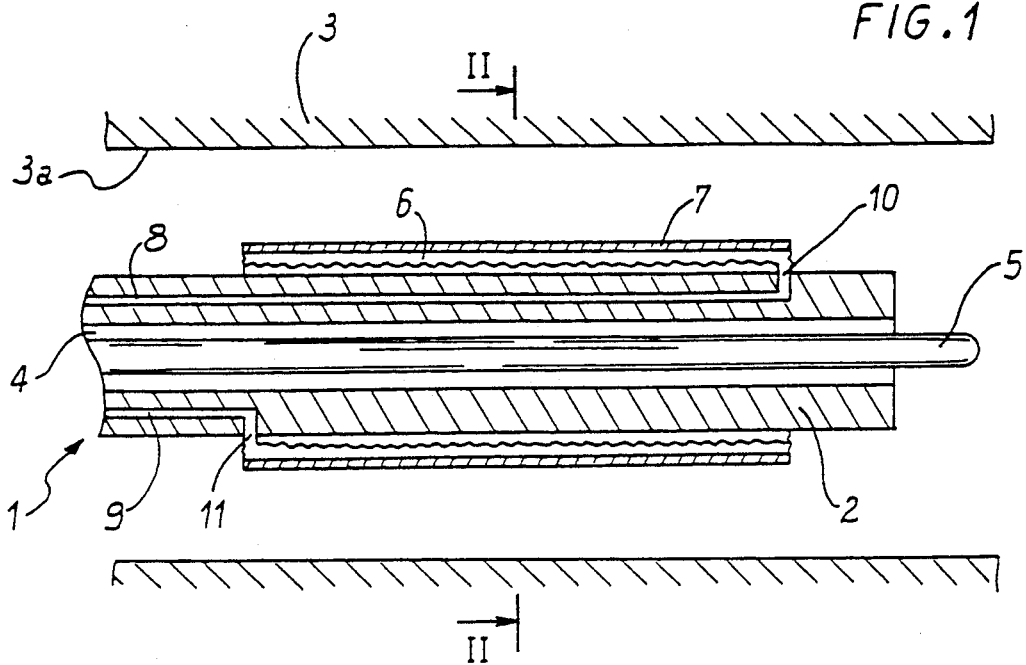
FIG. 1 is a schematic longitudinal section illustrating the positioning of the deflated sleeve inside a morphological duct.
Figure 3:
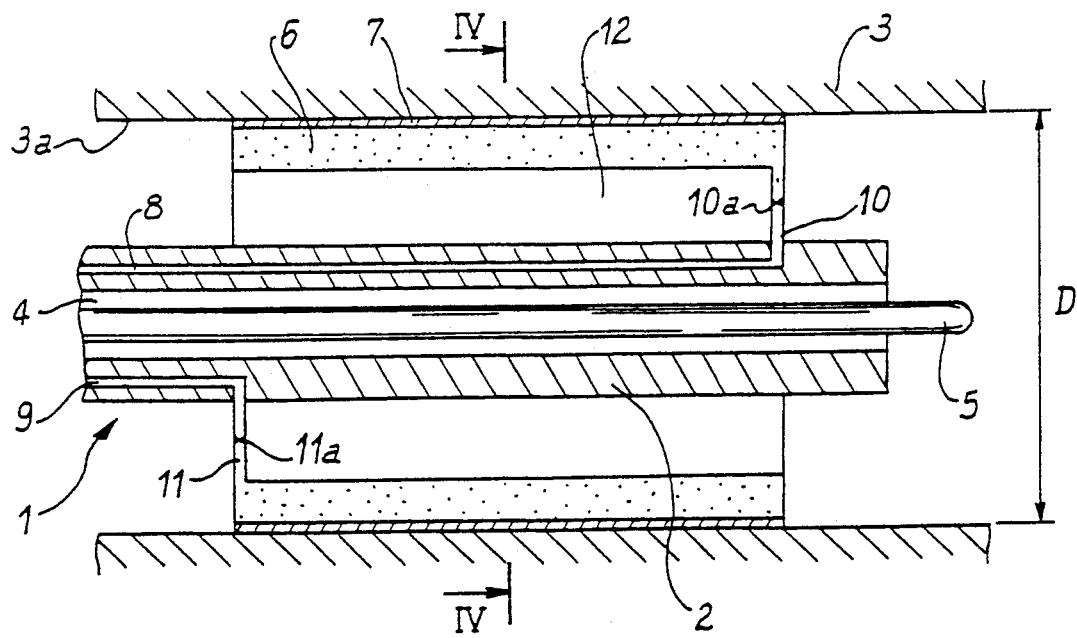
FIG. 3 is a schematic longitudinal section illustrating the positioning of the inflated sleeve inside a morphological duct.

The catheter 1, whose distal end 2 is shown in FIGS. 1 to 4, is introduced into a morphological duct 3, for example an artery. This catheter 1, which is shown in the form of a tube, has a longitudinal passage 4 therethrough in which is disposed a guide support 5 for introducing said catheter 1 inside the morphological duct 3 according to a well known technique.

The distal end 2 of catheter 1 is surrounded by an inflatable sleeve 6, itself compressed in the direction of said distal end 2 by a resilient membrane 7.

In the wall of catheter 1 are provided at least two conduits 8 and 9, connected respectively to said inflatable sleeve 6 by flexible connections 10 and 11. The proximal end (not shown) of conduit 8 is connected to an inflating device (not shown either) able to feed inflating fluid inside sleeve 6, for example gas or a liquid at a pressure of 2 or 3 bars, via said conduit 8 and the flexible connection 10. Thus, the fluid penetrating into the sleeve may leave through the flexible connection 11 and conduit 9, so that said fluid sweeps the sleeve. By controlling the flowrate of said fluid at the proximal end (not shown) of conduit 9, the pressure inside said sleeve may be regulated.

With sleeve 6 in the deflated state and compressed by the resilient membrane 7 (FIGS. 1 and 2), the catheter 1 is introduced into the morphological duct 3, by means of the guide support 5, and is positioned accurately by means of radio-opaque markers (not shown).

When sleeve 6 is thus brought to the desired location in the morphological duct 3, inflating fluid is fed to sleeve 6, in the way described above. Sleeve 6 then expands until its external wall covered by membrane 7 is applied against the internal wall 3a of the morphological duct 3, an annular space 12 then being formed between said sleeve 6 and the distal end 2 of catheter 1 (see FIGS. 3 and 4).

In this inflated state, sleeve 6 remains connected to conduits 8 and 9, via the flexible connections 10 and 11 which pass through said space 12.

Experience has shown that, in order to obtain good adhesion of sleeve 6 on the internal wall 3a of the morphological duct 3, it was sufficient for the pressure of the inflating fluid to be from 2 to 3 bars, which pressure can be tolerated by a patient. For this, in addition, it is advantageous for the diameter D of the morphological duct 3 to be less, for example by about 10%, than the external diameter which the sleeve 6 would have at its pressure of use inside said inflated duct 3, if it were not enclosed in the morphological duct 3.

In the case where sleeve 6 is to form a temporary prosthesis, the simple flow of fluid through sleeve 6 may maintain the rigidity thereof in the inflated state.

On the other hand, when sleeve 6 is to form a permanent prosthesis, the inflating fluid may be a resin (acrylic, epoxy) or a latex which is preferably polymerizable at ambient temperature. After polymerization of said fluid, the sleeve keeps its rigid inflated shape.

It is then preferable to provide on the flexible connections 10 and 11 weakened zones 10a and 11a, respectively, for breaking said connections, for example by twisting and/or pulling by the catheter 1. After breakage of said weakened zones 10a and 11a, the catheter 1 may be withdrawn from the morphological duct 3, only the rigid inflated sleeve 6 remaining in position.

The polymerization of sleeve 6 in the inflated state may also be obtained by introducing into sleeve 6 a material which, by reaction with the inflating fluid, is able to make the inflated sleeve rigid.

Of course, whatever the method of making the inflated sleeve rigid, solidification must take in a short time so as to minimize the intervention time.

In the case of a permanent prosthesis with rigidifiable sleeve, the catheter 1 will be of disposable type, for the inflating fluid will also be solidified in conduits 8 and 9.

It will be noted that, in some cases, the guide support 5 may be replaced, during the operation, by an optical fiber able to transmit radiation energy or by a tube coated with an inner coating for the transmission of ultra-sounds from an external source to the part to be treated.

The inflatable sleeve 6 may be formed in different ways. Preferably, it is made from a pre-formable material, such as an irradiated polyethylene. Thus, its shape in the inflated state may be adapted to that of the location of duct 3, where it is intended to form a prosthesis.

In the embodiment illustrated in FIG. 5, sleeve 6 comprises a flat pre-formed tube 13 wound in a helical coil. It will be noted that this embodiment is advantageous for, between the non jointing turns of the coil, sleeve 6 has spaces 14 through which the blood may flow. Thus, if the sleeve is disposed in a duct 3, at the intersection with one or more other morphological ducts, the blood may continue to flow between these ducts, through spaces 14. For this, it is necessary for membrane 7 to be itself perforated or, better still, have the form of a net. Of course, the sleeve may be formed of several helical coils with interfitting turns, having independent inflating inlets and outlets. These coils may have different diameters and internal and external communications may be provided between said coils.

In FIG. 6, sleeve 6 is formed by two welded walls 15 and 16, apertures 17 being formed in the side-wall of said sleeve for providing peripheral blood flow through the double wall of said sleeve.

The edges of apertures 17 are sealed to prevent escape of inflating fluid supplied through connections 10 and 11, or the entry of external fluid into the interior of sleeve 6.

Of course, whatever its embodiment, the sleeve 6 is made from a biocompatible material.

What is claimed is:

1. Catheter for a morphological duct comprising an inflatable sleeve having an external wall and an internal wall, said sleeve surrounding the distal end of said catheter and connected thereto by a first flexible connection, said first flexible connection being itself connected to the proximal end of said catheter by at least one inflating conduit which can be connected to an inflating device and said inflatable sleeve may take on either a deflated state in which its internal wall is applied against said distal end of said catheter, or an inflated state in which its external wall bears against the internal wall of said morphological duct, forming an annular space between the internal wall of said inflatable sleeve and said distal end of said catheter, wherein said inflating device feeds inflating fluid capable of making said sleeve rigid in its inflated state and said first flexible connection is breakable.

2. The catheter as claimed in claim 1, further comprising a resilient membrane surrounding said sleeve and compressing its against said distal end of the catheter.

3. The catheter as claimed in claim 2, wherein said resilient membrane is perforated.

4. The catheter as claimed in claim 1, further comprising a draining conduit connecting said sleeve to the proximal end of the catheter, by means of a second flexible connection connecting said sleeve to the distal end of said catheter, wherein said second flexible connection is breakable.

5. The catheter as claimed in claim 1, wherein said sleeve is formed by a tube wound in a helical coil.

6. The catheter as claimed in claim 5, wherein the turns of said coil are not jointing.

7. The catheter as claimed in claim 1, wherein said sleeve is a double-walled tube.

8. The catheter as claimed in claim 7, wherein said double-walled tube is formed with lateral openings which are sealed against entry of fluid to the interior of said tube.

9. The catheter as claimed in claim 1, wherein said sleeve is pre-formed.

10. The catheter as claimed in claim 9, wherein the external diameter of said sleeve, inflated out of said morphological duct to the pressure of use thereinside, is greater by about 10% than the diameter of said morphological duct.

* * * * *

UNITED STATES PATENT AND TRADEMARK OFFICE
CERTIFICATE OF CORRECTION

PATENT NO. : 5,312,339

DATED : May 17, 1994

INVENTOR(S) : GEORGES BOUSSIGNAC ET AL.

It is certified that error appears in the above-identified patent and that said Letters Patent is hereby corrected as shown below:

Title page, item [30], "Foreign Application Priority Data," the reference to "[JP] Japan" should be --[FR] France--.

Signed and Sealed this

Sixteenth Day of August, 1994

Attest:

BRUCE LEHMAN

*Attesting Officer*  *Commissioner of Patents and Trademarks*